United States Patent [19]

Richardson et al.

[11] Patent Number: 5,409,113
[45] Date of Patent: * Apr. 25, 1995

[54] NEEDLE DISPOSAL CONTAINER AND DISPOSAL SYSTEM

[75] Inventors: Michael R. Richardson, Crystal Lake; Lawrence G. Ponsi, Wheeling; Paul H. Hanifl, Barrington Hills, all of Ill.

[73] Assignee: Sage Products, Inc., Crystal Lake, Ill.

[*] Notice: The portion of the term of this patent subsequent to Jun. 21, 2011 has been disclaimed.

[21] Appl. No.: 209,608

[22] Filed: Mar. 10, 1994

Related U.S. Application Data

[63] Continuation of Ser. No. 5,638, Jan. 19, 1993, abandoned.

[51] Int. Cl.⁶ .............................................. B65D 83/10
[52] U.S. Cl. ..................................... 206/366; 206/365
[58] Field of Search ............. 206/366, 365, 370, 63.5; 220/908; 128/763, 770; 604/240

[56] References Cited

U.S. PATENT DOCUMENTS

| | | | |
|---|---|---|---|
| 3,746,155 | 7/1973 | Seeley | 206/365 |
| 4,375,849 | 3/1983 | Hanifl | 206/63.5 X |
| 4,494,652 | 1/1985 | Nelson et al. | 206/370 X |
| 4,520,926 | 6/1985 | Nelson | 206/370 X |
| 4,576,281 | 3/1986 | Kirksey | 206/370 |
| 4,841,985 | 6/1989 | Wanamaker | 604/240 |
| 4,867,309 | 9/1989 | Germain | 206/366 |
| 4,869,366 | 9/1989 | Bruno | 206/370 |
| 4,874,103 | 10/1989 | Quisenberry et al. | 220/908 X |
| 4,984,580 | 1/1991 | Wanamaker | 604/240 X |
| 4,995,871 | 2/1991 | Sasaki et al. | 206/366 X |
| 5,067,949 | 11/1991 | Freundlich et al. | 206/366 X |
| 5,090,564 | 2/1992 | Chimienti | 206/365 |
| 5,092,462 | 3/1992 | Sagstetter et al. | 206/366 |
| 5,117,837 | 6/1992 | Wanamaker et al. | 604/240 X |
| 5,188,598 | 2/1993 | Thead et al. | 206/366 X |
| 5,322,164 | 6/1994 | Richardson et al. | 206/366 |

FOREIGN PATENT DOCUMENTS 2740355  3/1979  Germany ............................ 206/366

OTHER PUBLICATIONS

UK Patent Application GB 2040268A, 28 Aug. 1980 (Elisha).

*Primary Examiner*—Paul T. Sewell
*Assistant Examiner*—Ted Kavanaugh
*Attorney, Agent, or Firm*—Lee, Mann, Smith, McWilliams, Sweeney & Ohlson

[57] ABSTRACT

A disposal container for automatic release of cannulas from a holder and for disposal of the cannulas, and a system for hands-free release of a cannula from a holder. Included is a disposal container having a release aperture formed in the top, the aperture including opposite tapered sides extending into the container. A cannula is mounted in a cannula holder, the holder having at least one depressible lock element extending from the holder. The holder is inserted in the release aperture with the lock element engaging the tapered side, and the holder is then depressed to automatically eject the cannula from the holder. If the cannula is installed in a removable adaptor inserted in the holder, both the adaptor and the cannula are ejected when the holder is depressed in the aperture.

15 Claims, 2 Drawing Sheets

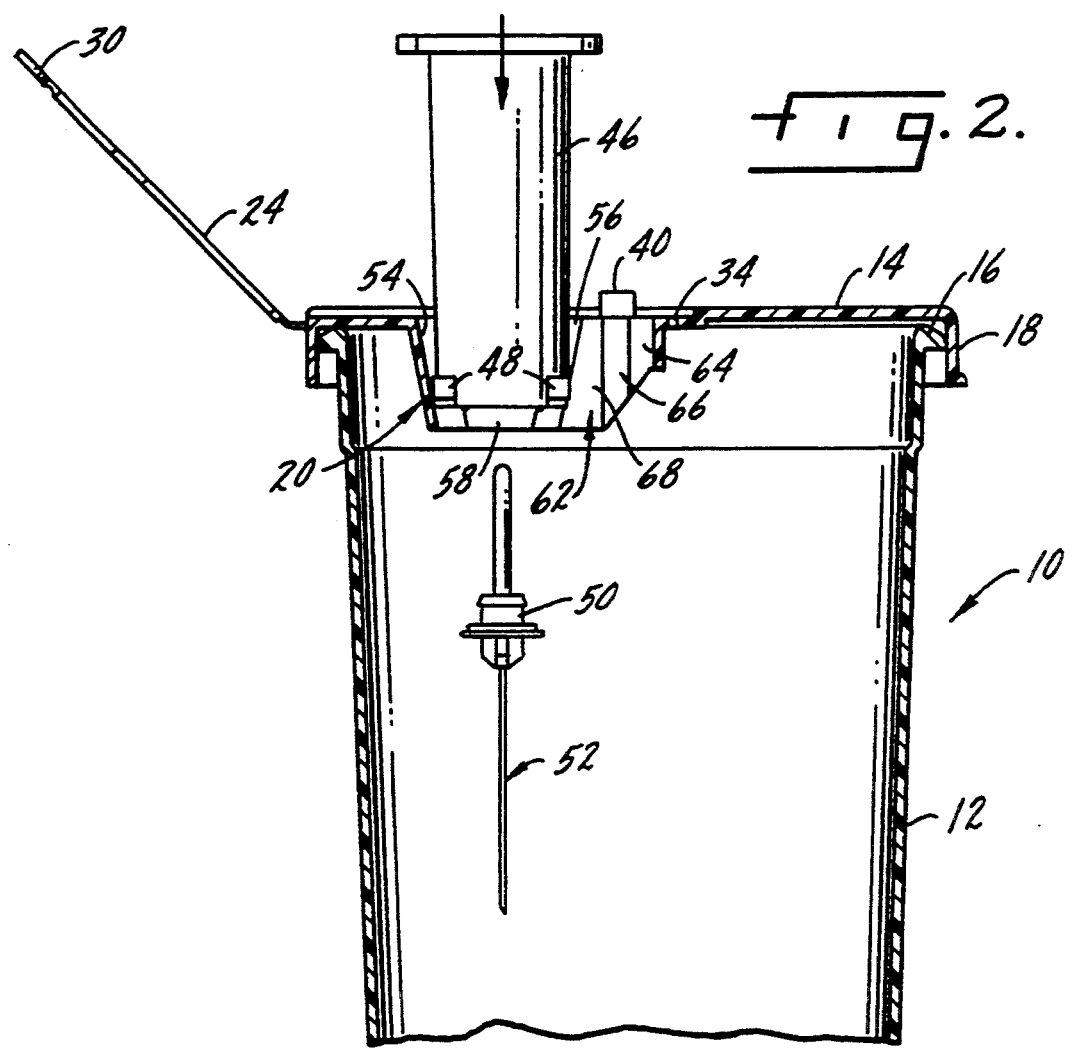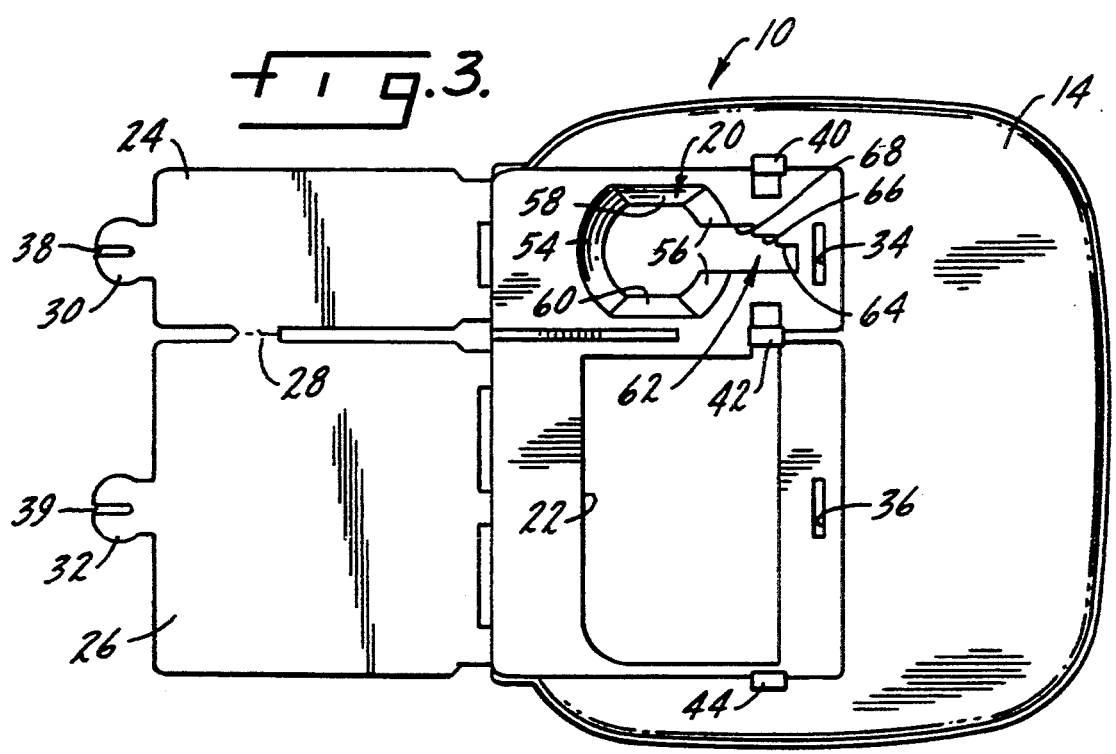

NEEDLE DISPOSAL CONTAINER AND DISPOSAL SYSTEM

This application is a continuation, of application Ser. No. 08/005,638, filed Jan. 19, 1993, now abandoned.

BACKGROUND OF THE INVENTION

This invention relates to needle disposal apparatus, and more particularly to a container and system for hands-free release of a cannula from a holder and disposal of the cannula.

As medical science has advanced, the sampling and analysis of a patient's blood has become an important diagnostic aid. However, blood collection can also pose hazards for the person drawing blood, and therefore various devices have been developed to protect the drawer as much as possible from contamination.

U.S. Pat. Nos. 4,841,985; 4,984,580 and 5,117,837 are directed to various developments in blood drawing apparatus, and the disclosures of said patents are incorporated herein by reference. In one form of the blood drawing apparatus of such patents, a disposable cannula adaptor is employed in connection with a holder for an evacuated blood collection tube. The cannula adaptor is inserted in one end of the holder and held temporarily in place, and a blood needle is then screwed into the adaptor, with one end extending outwardly for vein puncture, and an opposite end extending inwardly in the holder for piercing the blood collection tube. After use of the holder to collect blood, the cannula adaptor and cannula are released from the holder, and disposed. The holder can then be disposed, or cleaned and reused with a new cannula adaptor and cannula.

While the cannula adaptor concept of the incorporated patents provides a significant advance in blood drawing apparatus, the proper disposal of the soiled cannulas and cannula adaptors remains beyond the scope of the patents.

SUMMARY OF THE INVENTION

The invention provides a disposal container comprising a container body, a top of the container body, and a release aperture in the top. The release aperture includes opposite tapered sides, with the sides converging from an engagement position to an ejection position, with the ejection position being oriented into the container body.

In accordance with the preferred form of the invention, the tapered sides are curved, preferably in a concave fashion, toward one another, and the engagement position is proximate an upper surface of the top of the container. The ejection position is therefore located beneath the top within the container.

A closure is provided to selectively cover the release aperture. The closure preferably is pivotal, and includes means for locking the closure when it is closed. The locking means comprises a tab on the closure and a slot formed in the top of the container, with the slot being shaped to be engaged by and grip the tab when the closure is closed.

In addition, means is provided for temporarily retaining the closure in a closed position covering the release aperture. A pair of grip elements is provided extending from the top, with the grip elements being located on opposite sides of the closure and being spaced apart a distance commensurate to the width of the closure. The grip elements are shaped to engage and temporarily hold the closure when the closure is closed across the release aperture.

In accordance with the preferred form of the invention, a needle detaching device is also formed in the release aperture. The detaching device comprises a slot having a varied gap dimension for accommodating varying sized hubs of needles. In accordance with the preferred form of the invention, the slot includes a series of stepped notches, each of which has a different gap dimension to engage a different size of needle hub.

In the system according to the invention for hands-free release of a cannula from a holder and disposal of the cannula, a cannula holder is provided with means for releasably mounting a cannula in the holder. The mounting means includes at least one depressible lock element extending from the holder. The depressible element is shaped to engage a tapered side of the release aperture so that, upon insertion of the holder into the release aperture, the lock element is depressed to release the cannula into the container. Preferably, a cannula adaptor is employed in the holder with a cannula screwed into the adaptor, and when the holder is inserted into the release aperture, both the cannula and adaptor are released from the holder into the container.

BRIEF DESCRIPTION OF THE DRAWINGS

The invention is described in greater detail in the following description of an example embodying the best mode of the invention, taken in conjunction with the drawing figures, in which:

FIG. 2 is a partial cross sectional side elevational view of the disposal container illustrated in FIG. 1, with the holder engaged in a release aperture and with the cannula falling from the holder after having been released, and FIG. 3 is a top plan view of the disposal container according to the invention.

DESCRIPTION OF AN EXAMPLE EMBODYING THE BEST MODE OF THE INVENTION

Figure 1:
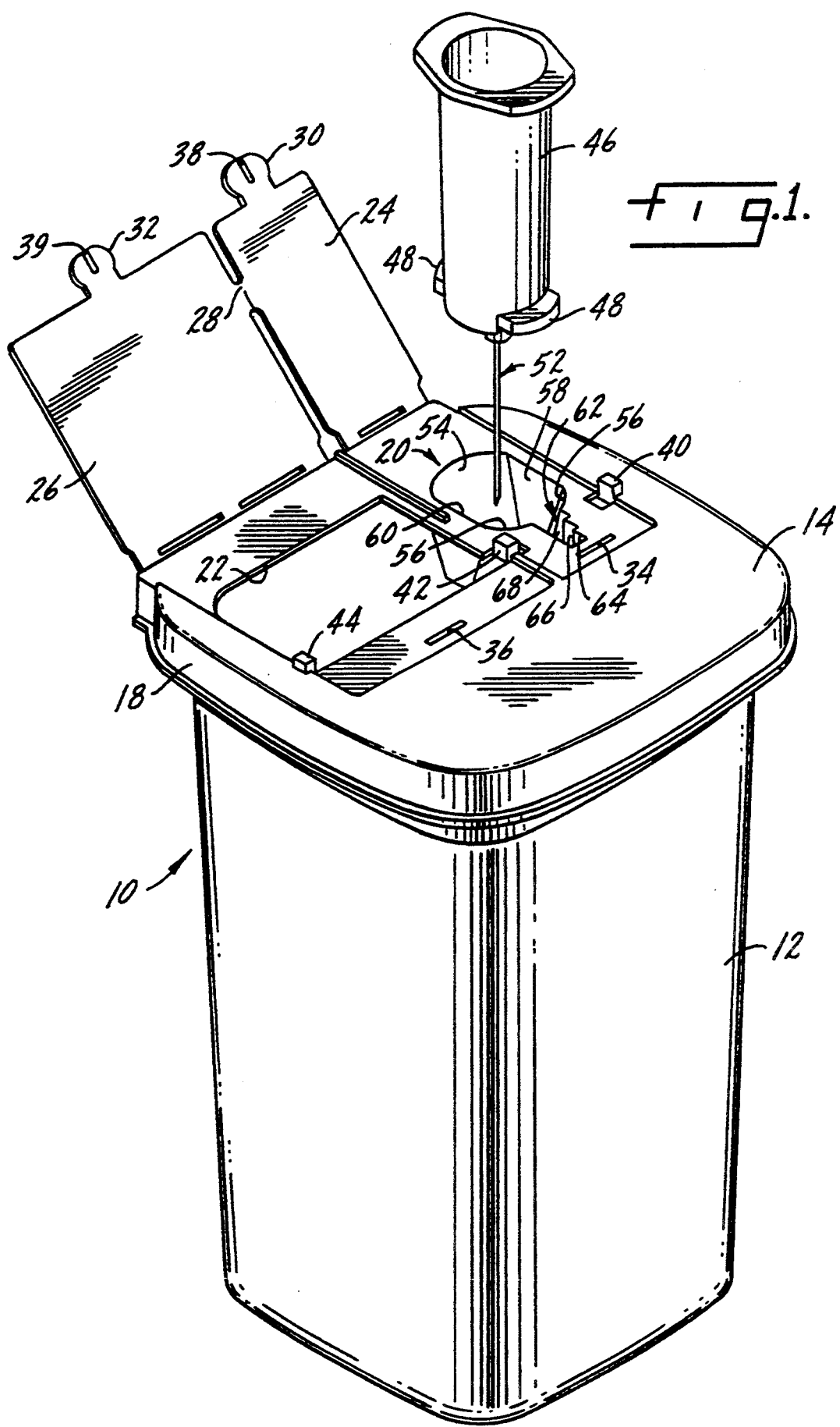
FIG. 1 is a perspective view of a disposal container according to the invention, with a holder and engaged cannula poised thereabove for release of the cannula from the holder.

A disposal container according to the invention is shown generally at 10 in the drawing figures. The container comprises two basic portions, a container body 12 and a top 14.

The container body 12 may be conventional, and includes an upper flange 16 shaped to be engaged beneath and hold the top 14. Various means of engagement (not illustrated) can be used, such as inwardly extending tabs extending from a skirt 18 of the top 14, the tabs being engaged beneath the flange 16. Other means of engagement can be employed, as well. It is preferred that the top 14 be relatively permanently applied to the container body 12, since needles discarded within the container 10 can be contaminated.

The top 14 includes a pair of apertures 20 and 22, with respective pivotal closures 24 and 26 poised to cover the apertures 20 and 22. A bridge 28 may be provided between the two closures so that the closures 24 and 26 can be operated in tandem. Since it is preferred that the container body 12 and top be formed of molded plastic, the bridge 28 is of the same material, and can be broken if desired to facilitate individual manipulation of the closures 24 and 26.

For permanent closing of the closures 24 and 26 across their respective apertures 20 and 22, each of the closures includes a respective tab 30 and 32. Corresponding slots 34 and 36 are formed in the top 14. Each of the tabs 30 and 32 includes a respective central cut 38 and 39, and the width of each of the tabs 30 and 32 is slightly greater than its corresponding slot 34 or 36 so that when a tab is inserted in a slot, the tab snaps into the slot, permanently closing the respective closure over its aperture. The cuts 38 and 39 allow the widths of the tabs 30 and 32 to be momentarily compressed while being inserted in the respective slots 34 and 36.

In addition to providing for permanently locking of the closures 24 and 26, also provided is means for temporarily closing the closures 24 and 26. Grip elements 40, 42 and 44 are formed in the top 14, the respective pairs of grip elements 40 and 42 and 42 and 44 being spaced apart a distance commensurate to the widths of the respective closures 24 and 26. The grip elements 40-44 have essentially upright, vertical sides so that when either or both of the closures 24 and 26 are pressed downwardly between the respective grip elements, the grip elements frictionally engage and temporarily hold the closures in place.

The aperture 22 is simply a relatively large opening into the container body 12. Items the size of the aperture 22 may therefore be inserted through the aperture 22. The aperture 20, however, is specifically sized and formed to function in conjunction with a cannula holder 46 of the nature described in incorporated U.S. Pat. No. 5,117,837, to which reference can be made for greater detail.

The cannula holder 46 includes opposite spring-loaded side locks 48. The side locks 48 are formed and shaped to releasably engage an adaptor 50 which, in turn, has internal threads formed to engage a cannula or blood needle 52. By depressing the opposite spring-loaded side locks 48, the adaptor 50 and blood needle 52 are released from the holder 46 as explained in the incorporated patents.

The aperture 20 includes opposite tapered sides 54 and 56 which, as best shown in FIGS. 2 and 3, are curved toward one another in a concave fashion. The curvatures of the tapered sides 54 and 56 match the curvature of the side locks 48 to positively engage the side locks 48, as explained in further detail below.

The aperture 20 also includes opposite straight sides 58 and 60. The straight sides 58 and 60 may also converge toward one another downwardly within the container body 12, as best shown in FIG. 3. Alternatively, the straight sides 58 and 60 can be essentially vertical in relation to the container 10 when upright on a flat surface.

While the aperture 20 is formed to release a cannula or blood needle 52 from a holder 46, a needle detaching device 62 may also be incorporated at one side of the aperture 20 for unscrewing of needles. The needle detaching device 62 is in the form of a slot bisecting the tapered side 56, and comprises a series of stepped notches 64, 66 and 68 each having a different gap dimension spanning the width of the slot of the detaching device 62. The detaching device 62 is formed and used as explained in greater detail in U.S. Pat. No. 4,375,849. Alternatively, instead of a series of steps, the detaching device 62 can be formed in a tapered configuration (thus with an "infinite" series of steps) to accommodate varying size needle hubs.

The aperture 20 is shown formed to work in conjunction with a holder 46 having a pair of side locks 48. Thus, each of the sides 54 and 56 is curved and tapered to function with the side locks 48 as a holder 46 is inserted in the aperture 20. The side locks 48 are first engaged at an engagement position proximate the upper surface of the top 14, and ejection occurs through an ejection positions formed at the bottoms of the converging sides 54-60. Because the opposite tapered sides 54 and 56 converge, various sized holders 46, given the spacing of the side locks 48, can be accommodated in a single container arrangement 10.

In use, as explained in greater detail in incorporated U.S. Pat. No. 5,117,837, an adaptor 50 is installed in the bottom of the holder 46. A blood needle 52 is then screwed into the adaptor, and the holder 46 and engaged blood needle 52 are used to withdraw blood from a patient in a normal fashion. Thereafter, to remove the adaptor 50 and the blood needle 52, the holder 46 is inserted within the aperture 20. As the side locks 48 engage the tapered sides 54 and 56, the side locks 48 are depressed, releasing the adaptor 50 and blood needle 52, causing them to drop within the container body 12 as shown in FIG. 2. Simple pushing on the top of the holder 46 causes the adaptor 50 and blood needle 52 to be disengaged by forcing the side locks 48 inwardly.

While the invention has been shown employing a holder 46 with a pair of side locks 48, different configurations can also be employed. A single lock element, rather than a pair of side locks 48, can function in connection with either or both of the tapered sides 54 and 56, and if a single locking element is employed, there need only be one tapered side 54 or 56. Also, the tapered sides 54 and 56, and side locks 48, are shown formed in a curved fashion corresponding to one another. Other shapes of side locks 48 can be employed, and the tapered sides 54 and 56 can be formed accordingly to accommodate those other shapes. Various other changes can be made to the invention without departing from the spirit thereof or scope of the following claims.

What is claimed is:

1. In a system for hands-free release of a cannula from a holder and disposal of the cannula, the system including a cannula holder and a disposal container for receipt of cannulas released from cannula holders, said cannula holder being engageable in said disposal container, said disposal container comprising
   a. a container body,
   b. a top on said container body, and
   c. a release aperture in said top, said release aperture including generally rigid opposite tapered sides, said sides being spaced a predetermined distance to and shaped to engage a depressible lock element of a said cannula holder and converging from an engagement position to an ejection position, said ejection position being oriented into said container body.

2. A disposal container according to claim 1 in which said sides are curved.

3. A disposal container according to claim 1 in which said sides are concave.

4. A disposal container according to claim 1 in which said engagement position is proximate an upper surface of said top and said ejection position is located beneath said top.

5. A disposal container according to claim 1 including a closure formed to selectively cover said aperture.

6. A disposal container according to claim 5 in which said closure is pivotal.

7. A disposal container according to claim 5 including means for locking said closure when said closure covers said aperture.

8. A disposal container according to claim 7 in which said locking means comprises a tab on said closure and a slot formed in said top, said slot being shaped to be engaged by and grip said tab.

9. A disposal container according to claim 5 including means for temporarily retaining said closure in a position covering said aperture.

10. A disposal container according to claim 9 in which said closure has a predetermined width and said means for temporarily retaining comprises a pair of grip elements extending from said top, said grip elements being located on opposite sides of said closure and being spaced apart a distance commensurate to said width, said grip elements being shaped to engage and temporarily hold said closure.

11. A disposal container according to claim 1 including a needle detaching device formed in said release aperture.

12. A disposal container according to claim 11 in which said detaching device comprises a slot having a varied gap dimension for accommodating varying sized hubs of needles.

13. A disposal container according to claim 12 in which said slot includes a series of stepped notches each having a different gap dimension.

14. A disposal container according to claim 1, including a second aperture in said top for disposal therethrough, said second aperture being larger in dimension than said release aperture.

15. A disposal container according to claim 14, including a closure formed to selectively cover said second aperture.

* * * * *